US00PP30228P3

(12) United States Plant Patent
Wirthensohn

(10) Patent No.: US PP30,228 P3
(45) Date of Patent: Feb. 26, 2019

(54) ALMOND VARIETY NAMED 'VELA'

(50) Latin Name: *Prunus dulcis*
Varietal Denomination: VELA

(71) Applicants: The University of Adelaide, Adelaide (AU); Horticulture Innovation Australia Ltd, Sydney (AU)

(72) Inventor: Michelle Wirthensohn, Adelaide (AU)

(73) Assignees: The University of Adelaide, Adelaide (AU); Horticulture Innovation Australia Ltd., Sydney (AU)

( * ) Notice: Subject to any disclaimer, the term of this patent is extended or adjusted under 35 U.S.C. 154(b) by 0 days.

(21) Appl. No.: 15/732,560

(22) Filed: Nov. 28, 2017

(65) Prior Publication Data

US 2018/0160579 P1 Jun. 7, 2018

(30) Foreign Application Priority Data

Dec. 2, 2016 (AU) ..... PBR 2016/346

(51) Int. Cl.
*A01H 5/08* (2018.01)
*A01H 6/74* (2018.01)

(52) U.S. Cl.
USPC ..... Plt./155
CPC ..... *A01H 5/08* (2013.01); *A01H 6/7427* (2018.05)

(58) Field of Classification Search
USPC ..... Plt./155
See application file for complete search history.

*Primary Examiner* — Annette H Para
(74) *Attorney, Agent, or Firm* — Marshall, Gerstein & Borun LLP

(57) ABSTRACT

A new and distinct almond variety of *Prunus dulcis* named 'VELA', particularly characterized by self-fertility, large kernels and very high production. Other desirable characteristics include medium to late harvest time, well-sealed soft shells, and high quality, sweet kernels with high oil content.

3 Drawing Sheets

Latin name of the genus and species of the plant claimed: *Prunus dulcis*.

Variety denomination: 'VELA'.

BACKGROUND OF THE INVENTION

The present invention relates to a new and distinct cultivar of almond varieties, botanically known as *Prunus dulcis*, and hereinafter referred to by the name 'VELA'.

The disclosure provides a new and distinct variety of almond tree, botanically known as *Prunus dulcis*, synonymous with *Prunus amygdalus* Batsch., *Amygdalus communis* L., and *Amygdalus dulcis* Mill., which belongs to the Rosaceae family, and is hereinafter referred to by the variety denomination 'VELA'.

The new *Prunus dulcis* variety is a product of a controlled breeding program conducted by the inventor Michelle Wirthensohn in Adelaide, Australia. The objective of the breeding program was to develop new almond varieties with high production, self-fertility and good kernel characteristics.

The new *Prunus dulcis* 'VELA' originated from a cross in 2002 in Adelaide, Australia. The female or seed parent is the Australian, *Prunus dulcis* variety designated 'Chellaston' (unpatented) and the male or pollen parent is the proprietary almond seedling with field identification number 'A97001-1bT47'. The pollen parent (A97001-1bT47) originated from a cross between 'Nonpareil' x 'Lauranne' and was chosen on the basis of kernel quality and self-fertility. The new *Prunus dulcis* 'VELA' was selected by the inventor from the progeny of the stated cross in field trials in 2013 in Lindsay Point, Australia. First observations occurred in 2007.

Asexual propagation of the new *Prunus dulcis* 'VELA' by grafting onto *Prunus persica* (L.) Batsch X *Prunus dulcis* rootstock designated 'GF677' (unpatented) was first performed in 2009 in the orchard located in Lindsay Point, Australia. Asexual propagation of the new *Prunus dulcis* 'VELA' has confirmed that the characteristics as herein disclosed for the new variety are stable and retained through successive generations of asexual propagation. The new variety propagates true-to-type.

Asexual reproduction of the new almond tree has shown that the unique features of this new almond tree are stable and reproduced true to type in successive generations of asexual reproduction.

SUMMARY OF THE INVENTION

The 'VELA' variety of almond is of medium size, similar to 'Nonpareil' (unpatented), medium vigor with upright to spreading growth and demonstrates very high and regular production of soft shell nuts with kernels having an excellent flavour similar to 'Nonpareil' (unpatented). The harvest maturity is later than 'Nonpareil' (unpatented) and the nuts release from the hulls readily. The percentage of doubles is very low, less than 1% under growing conditions in the Riverland area of South Australia. The tree is self-fertile and, therefore, is able to produce almonds without the use of pollinators.

The following traits have been repeatedly observed and are determined to be the unique characteristics which make the new variety 'VELA' clearly distinguishable from its parents and the variety most similar of common knowledge which is 'Nonpareil' (unpatented):

1. self-fertility;
2. high productivity; and
3. ease of harvest.

The following characteristics listed in Table 1 have been repeatedly observed in combination and distinguish 'VELA' as a new and distinct almond variety:

TABLE 1

| Trait | New variety 'VELA' | Female parent 'Chellaston' (unpatented) | Male parent 'A97001-1bT47' (unpatented) | Most similar variety of common knowledge 'Nonpareil' (unpatented) |
|---|---|---|---|---|
| Shell type | Soft | Soft | Hard | Paper |
| Tree habit | Upright-spreading | Slightly open | Slightly open | Slightly open |
| Self-fertility | Present | Absent | Present | Absent |
| Flowering time | Early-medium | Early | Medium | Early-medium |
| Kernel size | Large | Large | Small | Medium |
| Time of maturity | Medium-late | Early | Early-medium | Early |

Distinguishing characteristics of 'VELA' are set out in Table 1. Plants of the new 'VELA' almond tree have not been observed under all possible environmental conditions and cultural practices. The phenotype may vary somewhat with variations in environment, such as temperature, day length and light intensity, without, however, any variance in genotype.

The primary difference between the new variety and the female parent 'Chellaston' (unpatented) is the new variety is self-fertile and does not require a pollinator tree planted near to fertilize the flowers and, thus, produce almonds, and has a medium to late maturity date, whereas 'Chellaston' (unpatented) is self-sterile with an early harvest date. In comparison to its male parent 'A97001-1bT4' (unpatented), the new variety has larger fruit, and is soft-shelled.

The primary difference between the new variety and the most similar variety of common knowledge 'Nonpareil' (unpatented) is the new variety is self-fertile with large kernel size, whereas 'Nonpareil' (unpatented) is self-sterile, and medium kernel size.

BRIEF DESCRIPTION OF THE DRAWING

The accompanying photographs (drawings) illustrate the overall appearance of the new *Prunus dulcis* 'VELA' showing the colors, as true as is reasonably possible with digital reproduction. Colors in the photographs may differ slightly from the color values cited in the detailed botanical description, which accurately describe the color of 'VELA'. The trees were grown on GF677 rootstock.

DETAILED BOTANICAL DESCRIPTION

Figure 1A:
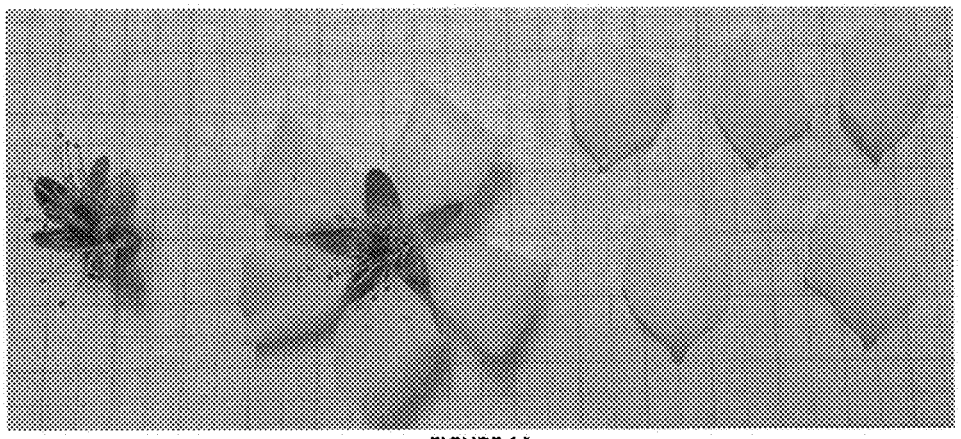
FIGS. 1A-1B show typical flowers of 'VELA', dissected (FIG. 1A) and flower buds in situ (FIG. 1B).
Figure 1B:
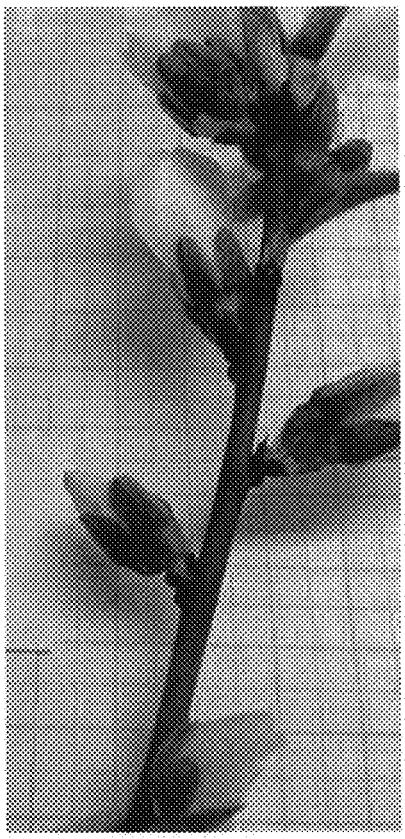
Figure 2A:
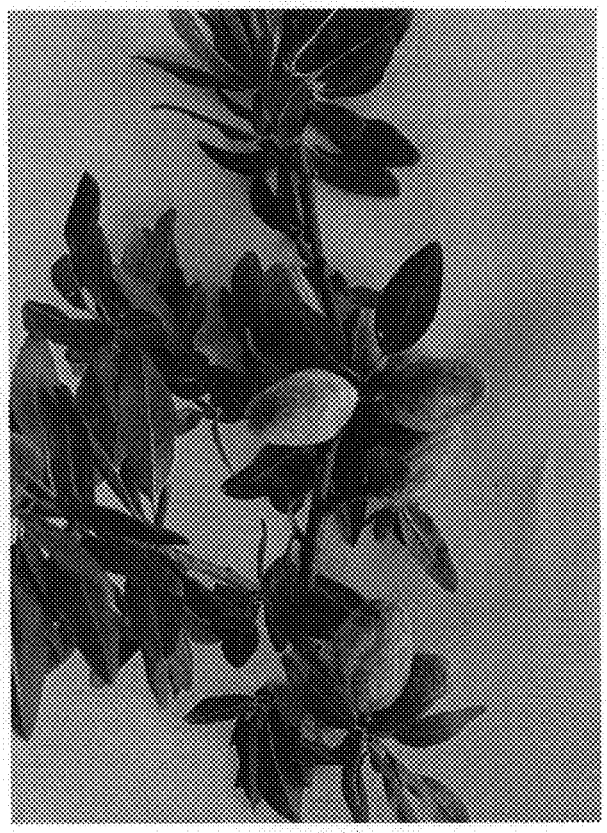
FIGS. 2A-2B show various images of fruit of 'VELA', including a one-year-old shoot, showing green immature fruit (FIG. 2A), and kernel and dry fruit shapes (FIG. 2B).
Figure 2B:
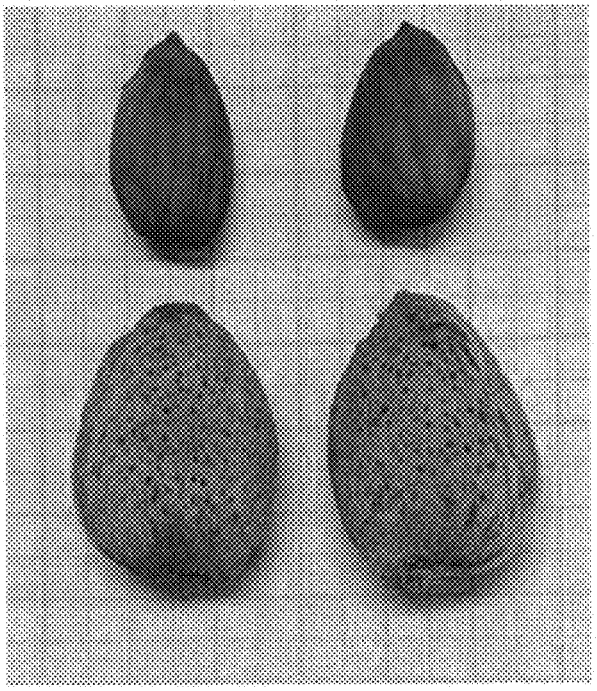
Figure 3:
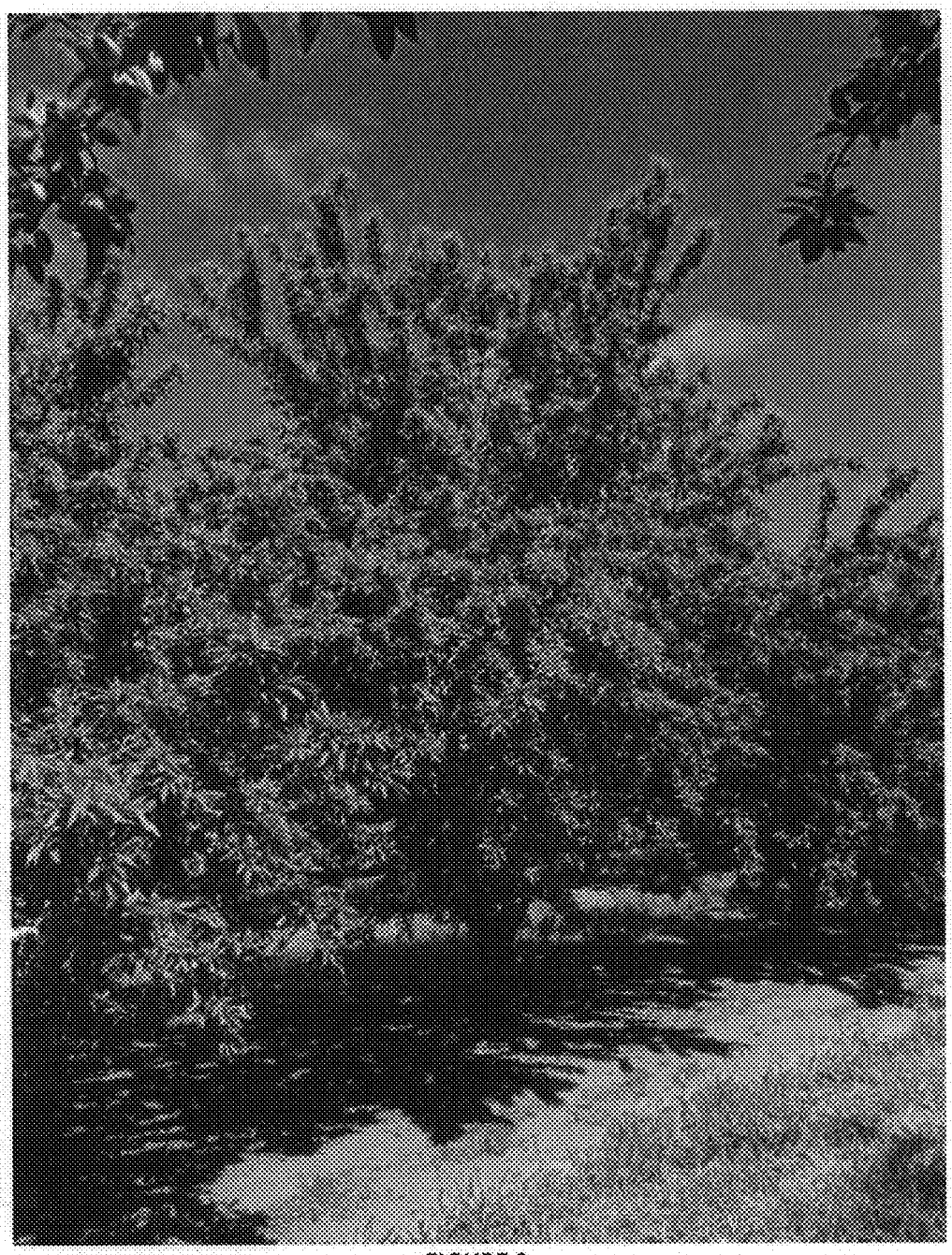
FIG. 3 shows a typical six-year-old tree of 'VELA' on 26 Oct. 2016.

Plants used in the aforementioned photographs and in the following description were grown outside under natural season conditions and cultural practices which approximate those generally used in commercial almond production. During the production of the plants, day temperatures ranged from about 14.5° C. to 48.2° C., night ranged from about −5.7° C. to 14° C. and light levels ranged from about 126,905 to 564,729 foot-candles. Measurements and numerical values represent averages for typical flowering plants.

The following is a detailed description of the new 'VELA' variety when observed during the growing seasons from 2011 to 2017 at Lindsay Point, Victoria, Australia. During 2017, the 'VELA' trees were seven years of age. Quantified measurements are expressed as an average of measurements taken from a number of trees of 'VELA'. The measurements of any individual tree (or any group of trees) of 'VELA' may vary from the stated average.

Color references are made to The Royal Horticultural Society Colour Chart (R.H.S.), sixth edition, (2015). Color values were taken under conditions of natural light.

All of the trees of 'VELA', insofar as they have been observed, have been consistent in the characteristics described below.

Classification:

*Botanical.*—*Prunus dulcis.*

Parentage:

*Female, or seed parent.*—*Prunus dulcis* Australian variety designated 'Chellaston', unpatented.

*Male, or pollen parent.*—Australian self-fertile *Prunus dulcis* proprietary seedling designated 'A97001-1bT47', unpatented.

Propagation:

*Type.*—Budding onto rootstock.

*Time to initiate roots.*—NA.

*Time to produce young plant.*—Eight months.

*Root description.*—'GF677' (unpatented) rootstock.

Plant description:

Tree:

*Height.*—About 4.5 to 5 m.

*Spread.*—To about 5 m.

*Size.*—Medium. Similar to Nonpareil. The height at six years of maturity is about 4.5 to 5 meters with a spread of about 4 meters.

*Vigor.*—Medium.

*Density.*—High.

*Habit.*—Upright to spreading.

Trunk:

*Diameter.*—About 62-69 cm, average about 65 cm at about 15 cm high.

*Texture.*—Slightly rough.

*Color of bark.*—RHS 200D, moderate brown.

*Lenticels length.*—About 1.9-2.9 mm, average about 2.26 mm.

*Lenticels width.*—About 0.7-1.5 mm, average about 1.07 mm.

*Lenticels density.*—About 15 per $cm^2$ on seven year-old wood.

*Lenticels shape.*—Narrow elliptic.

*Lenticels color.*—RHS 200C, moderate brown.

Current season shoot:

*Texture.*—Smooth.

*Shape in cross section.*—Round.

*Color.*—RHS 143B, strong yellow green.

Mature wood:

*Color.*—RHS 200B, greyish reddish brown.

One year-old shoot:

*Texture.*—Smooth.

*Thickness*.—Thick to very thick, about 4-6.6 mm, average about 5.45 mm.
*Length*.—Up to about 96 cm.
*Internode length*.—About 0.7-2.0 cm, average about 1.35 cm.
*Shape in cross section*.—Round.
*Color*.—RHS N197A, light olive grey.
*Anthocyanin coloration*.—RHS 176A, greyish red on top, 144A, strong yellow green on underside.
*Intensity of anthocyanin coloration*.—Weak on sunny side.
*Internode length*.—About 0.7-2.0 cm.
*Feathering*.—Medium.
*Lenticels length*.—About 0.7-1.5 mm, average about 0.97 mm.
*Lenticels width*.—About 0.4-1.5 mm, average about 0.45 mm.
*Lenticels density*.—About 19 per $cm^2$.
*Lenticels shape*.—Narrow elliptic.
*Lenticels color*.—RHS 164A, brownish orange.

Foliage:
*Density*.—Dense.

Leaf blade:
*Length*.—About 65-105 mm, average about 79.9 mm.
*Width*.—About 21-35 mm, average about 26.5 mm.
*Length/width ratio*.—Low to medium.
*Shape*.—Elliptic.
*Shape of base*.—Broad wedged-shaped convex.
*Shape of apex*.—Acute.
*Color of upper surface*.—RHS NN137B, greyish olive green.
*Color of lower surface*.—RHS 137B, moderate olive green.
*Incisions of margin*.—Crenate.
*Venation type*.—Arcuate.
*Venation color on underside*.—RHS 157A, pale yellow green.
*Venation color on upperside*.—RHS 157A, pale yellow green.
*Leaf gland number*.—About 0-4, located on upper portion of petiole and base of leaf blade.
*Leaf gland shape*.—Globose.
*Leaf gland diameter*.—About 0.5-0.7 mm.
*Leaf gland color*.—RHS 200D, moderate brown.

Leaf glands:
*Leaf gland number*.—About 0-4, located on upper portion of petiole and base of leaf blade.
*Leaf gland shape*.—Globose.
*Leaf gland diameter*.—About 0.5-0.7 mm.
*Leaf gland color*.—RHS 200D, moderate brown on both surfaces.

Petiole:
*Length*.—About 19-30 mm, average about 23.7 mm.
*Diameter*.—About 0.5-0.7 mm.
*Color on upper surface*.—RHS 137C, moderate yellow green.
*Color on lower surface*.—RHS 145C, light yellow green.
*Shape in cross section*.—Concave.

Spurs:
*Shape*.—Cylindrical.
*Length*.—About 11-37 mm, average about 21.7 mm.
*Diameter*.—About 3.3-4.2 mm, average about 3.79 mm.
*Color*.—RHS 200B, greyish reddish brown.

Flower buds:
*Distribution*.—Equally on spurs and one-year-old wood.
*Shape of lateral bud*.—Triangular.
*Shape of terminal bud*.—Triangular.
*Length of lateral bud*.—About 6.3-9.2 mm, average about 8 mm.
*Length of terminal bud*.—About 6.3-8.1 mm, average about 7.25 mm.
*Diameter of lateral bud*.—About 3.3 to 4.6 mm, average about 3.69 mm.
*Diameter of terminal bud*.—About 3.1 to 3.8 mm, average about 3.3 mm.
*Color of lateral bud*.—RHS 200C, moderate brown.
*Color of terminal bud*.—RHS 175A, moderate reddish brown.
*Color of tip of petals*.—RHS 62D, pale purplish pink.
*Color of sepals*.—RHS 183B, dark red.
*Hairiness of sepals*.—Absent or very weak.

Sepals:
*Number*.—Five.
*Shape*.—Broad elliptic.
*Length*.—About 6.7-7.8 mm, average about 7.1 mm.
*Width*.—About 3.1-5.3 mm, average about 4.2 mm.
*Apex*.—Rounded.
*Margin description*.—Medium to strong hairiness.
*Color outer*.—RHS 138A, moderate yellowish green to 187B, dark red anthocyanin.
*Color inner*.—RHS 138A, moderate yellowish green with nectary color 28A, vivid yellowish pink.

Pedicels:
*Length*.—About 4.3-7.9 mm, average about 5.95 mm.
*Color*.—RHS 144A, strong yellow green.

Flower:
*Description*.—Occurs in singles or clusters, petal bases becoming red when mature, strong fragrance.
*Size*.—Medium to large.
*Diameter*.—About 36-50 mm, average about 45.2 mm.
*Shape of petals*.—Medium elliptic.
*Undulation of margin*.—Medium.
*Shape of apex*.—Retuse, indented.
*Shape of base*.—Acute.
*Number of petals*.—Five.
*Color of petals on inner surface*.—RHS N155D, yellowish white.
*Color of petals on outer surface*.—RHS NN155C, white.
*Number of pistils*.—One.

Stamen:
*Number of stamens*.—Medium, about 21-38, average about 29.8.
*Anthocyanin coloration of filament*.—Absent or weak.

Pollen:
*Pollen amount*.—Moderate.
*Pollen color*.—RHS 153D, strong yellow.

Stigma:
*Position of stigma in relation to anthers*.—Below.
*Size*.—Medium.

Green fruit:
*Size*.—Medium to large.
*Shape*.—Ovate.
*Shape of apex*.—Rounded.
*Pubescence*.—Dense.
*Length*.—About 39.62 mm (average).
*Width*.—About 31.47 mm (average).

*Thickness*.—About 26.0 mm (average).
*Color*.—RHS N148B, moderate yellow green.
*Leaves per spur*.—About 12.73.

Dry fruit:
*Shape*.—Elliptic.
*Shape of apex*.—Acute.
*Shape of base*.—Flat to weakly cordate.
*Length*.—Short to medium, about 32-36 mm, average about 34.05 mm.
*Width*.—Narrow to medium, about 22-25 mm, average about 23.02 mm.
*Ratio length/width*.—Elongated, about 1.48.
*Thickness*.—About 14-18 mm, average about 16.4 mm.
*Average weight*.—About 3.29 g.
*Color of outer surface*.—RHS 164B, moderate orange yellow.
*Color of inner surface*.—RHS 164C, moderate orange yellow.
*Surface*.—Smooth with moderate pitting.
*Thickness of endocarp*.—Medium, about 1.8-3 mm, average about 2.4 mm.
*Resistance to cracking*.—Low, softshell.
*Percentage of kernel to dry fruit*.—Approximately 55%.
*Keel development*.—Strong.
*Distribution on tree*.—On spurs and one year-old shoots.

Fruit:
*Percentage of double kernels*.—This variety does not produce double kernels in the Australian production zones.
*Production*.—Regular. Yield at seven years old is about 3,927 kg/ha.
*Eating quality*.—Excellent. Oil content average is about 57.2%.

Kernel:
*Shape*.—Broad elliptic.
*Size*.—Large to very large.
*Average weight*.—About 1.83 g.
*Length*.—About 26-29 mm, average about 27.3 mm.
*Width*.—About 14-16 mm, average about 14.6 mm.
*Thickness*.—About 9-10 mm, average about 9.6 mm.
*Shape of apex*.—Acuminate with short tip.
*Shape of base*.—Rounded.
*Main color*.—RHS 164B, moderate orange yellow.
*Intensity of color*.—Light.
*Rugosity*.—Weak to medium.
*Taste*.—Sweet.

Blooming/flowering timing:
*Time of beginning of flowering*.—Early to medium, one day before 'Nonpareil'. During August (winter in Australia).
*Time of leaf budburst in relation to beginning of flowering*.—From about one week before to simultaneous.
*Flowering period*.—Up to about three weeks, depending on the weather. Full bloom in 2016 was about 16$^{th}$ August (in Australia).
*Time of maturity*.—Medium to late. Seven and one half months to maturity from beginning of flowering, from August to early March (in Australia).
*Peak harvest*.—Late summer (in Australia), approximately 10 days after Nonpareil.

Cultural characteristics:
*Susceptibility to disease*.—Very good tolerance to bacterial spot.
*Susceptibility to pests*.—No specific testing has been done.
*Storage/shipping*.—Good, comparable to Nonpareil (unpatented).

We claim:

1. A new and distinct variety of almond tree (*Prunus dulcis*) named 'VELA', as illustrated and described herein.

* * * * *